United States Patent [19]
Fan et al.

[11] Patent Number: 5,681,815
[45] Date of Patent: Oct. 28, 1997

[54] ANTIVIRAL AND ANTITUMOR AGENTS

[75] Inventors: Sophie Fan, Millwood, N.Y.; Xuhui Wang, Shanghai, China

[73] Assignee: Sophie Chen, Millwood, N.Y.

[21] Appl. No.: 83,949

[22] Filed: Jun. 28, 1993

[51] Int. Cl.$^6$ ................................................. A61K 38/00
[52] U.S. Cl. .................................... 514/12; 530/324
[58] Field of Search ................... 530/324, 342; 514/12

[56] References Cited

U.S. PATENT DOCUMENTS

| | | | |
|---|---|---|---|
| 3,849,252 | 11/1974 | Percs et al. ................................ | 195/62 |
| 3,950,547 | 4/1976 | Lamar et al. ................................ | 426/74 |
| 5,532,214 | 7/1996 | Lee-Huang et al. ......................... | 214/2 |

OTHER PUBLICATIONS

Sokolov, N.N., Fitsner, A.B., Anikeicheva, N.V. Kovalenko, N.A.; Role of Divalent Cations In The Endonucleolysis of DNA Catalyzed by Restrictases; Inst. Med. Enzymol., Moscow, USSR; VOPR. Med. Khim. (1989), 35(6) (Abstract only) Coden: VMDKAM; ISSN: 0042-8809.

Li et al., Nucleic Acids Research, vol. 19, No. 22, pp. 6309–6312 (1991).

Yu et al., Pure & Appl. Chem., vol. 58, No. 5, pp. 789–796, (1986).

*Primary Examiner*—Cecilia J. Tsang
*Assistant Examiner*—Kent L. Bell
*Attorney, Agent, or Firm*—Charles J. Herron

[57] ABSTRACT

The present invention relates to polypeptide-containing compound(s), composition(s) comprising such compound(s) along with divalent metal ions and/or a carbohydrate moiety, their antiviral and anti-hepatoma activities, and the enhancement of activity of antiviral polypeptide-containing agents by their combination with a carbohydrate and at least one divalent metal ion. Preferably, the carbohydrate is a polysaccharide of arabinose and galactose and, independently, the at least one divalent metal ion(s) include magnesium and zinc. The carbohydrate and divalent metal ion can be present in the form of a complex. The composition has been isolated and purified from the root tubers of the Chinese plant, Zei-Bai.

7 Claims, No Drawings

ANTIVIRAL AND ANTITUMOR AGENTS

The present invention relates to polypeptide-containing compound(s) (hereinafter "PROTEINA"), composition(s) comprising such compound(s) along with divalent metal ions and/or a carbohydrate moiety (hereinafter "ALICIN"), their antiviral and anti-hepatoma activities, and the enhancement of activity of antiviral polypeptide-containing agents by their combination with a carbohydrate and at least one divalent metal ion. Preferably, the carbohydrate is a polysaccharide that consists essentially of arabinose and galactose and, independently, the at least one divalent metal ion consists essentially of magnesium and zinc. The carbohydrate and divalent metal ion can be present in the form of a complex.

Thus, in one principal aspect, the invention relates to a composition comprising an amino acid-containing compound having the formula:

```
R—Thr—R—Gly—Asn—Tyr—R—Arg—Leu—R—Ala—Gly—
R—Leu—Arg—Glu—Asn—Ile—R—Leu—Gly—R—Leu—R—Ala—
Ile—R—Leu—R—Tyr—Tyr—R—Ile—Gln—R—Ser—Glu—Ala—
Ala—Arg—R—Ile—Glu—R—Arg—R—Ile—R—Asn—R—Gly—R—
Phe—R—Ser—Pro—R—Leu—R
``` wherein each R is independently at least one amino acid or analog thereof. Preferably, the compound has the formula:

```
Xaa—Xaa—Xaa—Thr—Xaa—Xaa—Xaa—Xaa—Gly—Asn—Tyr—
Xaa—Arg—Leu—Xaa—Xaa—Xaa—Ala—Gly—Xaa—Leu—Arg—
Glu—Asn—Ile—Xaa—Leu—Gly—Xaa—Xaa—Xaa—Leu—Xaa—
Xaa—Ala—Ile—Xaa—Xaa—Leu—Xaa—Tyr—Tyr—Xaa—Xaa—Xaa—
Xaa—Xaa—Xaa—Xaa—Xaa—Xaa—Xaa—Xaa—Xaa—Ile—Gln—
Xaa—Xaa—Ser—Glu—Ala—Ala—Arg—Xaa—Xaa—Xaa—Ile—Glu—
Xaa—Xaa—Xaa—Xaa—Xaa—Arg—Xaa—Xaa—Xaa—Xaa—Xaa—
Xaa—Xaa—Xaa—Xaa—Xaa—Xaa—Xaa—Xaa—Xaa—Xaa—Xaa—
Xaa—Xaa—Xaa—Xaa—Xaa—Xaa—Xaa—Xaa—Xaa—Xaa—Xaa—
Ile—Xaa—Xaa—Xaa—Asn—Xaa—Gly—Xaa—Phe—Xaa—Ser—Pro—
Xaa—Xaa—Leu—Xaa—Xaa—Xaa—Xaa—Xaa—Xaa—Xaa—Xaa—
Xaa—Xaa—
``` wherein each Xaa is independently a substantially homologous spacer or linker formed of at least one amino acid or analog thereof. Usually, each R is independently one or more amino acids. In a particularly preferred embodiment, the amino acid-containing compound has the formula:

```
Arg-Lys-Val-Thr-Leu-Pro-Tyr-Ser-Gly-Asn-Tyr-Glu-Arg-Leu-
Gln-Thr-Ala-Ala-Gly-Gly-Leu-Arg-Glu-Asn-Ile-Pro-Leu-Gly-
Leu-Pro-Ala-Leu-Asp-Ser-Ala-Ile-Thr-Thr-Leu-Phe-Tyr-Tyr-
Asn-Ala-Asn-Ser-Ala-Ala-Ser-Ala-Leu-His-Val-Leu-Ile-Gln-
Ser-Thr-Ser-Glu-Ala-Ala-Arg-Tyr-Lys-Phe-Ile-Glu-Gln-Gln-
Ile-Gly-Ser-Arg-Val-Asp-Lys-Thr-Phe-Leu-Pro-Ser-Leu-Ala-
Ile-Ile-Ser-Leu-Glu-Asn-Ser-Leu-Trp-Leu-Ala-Leu-Ser-Lys-
Gln-Ile-Gln-Ile-Ala-Ser-Thr-Asn-Asn-Gly-Thr-Phe-Glu-Ser-
Pro-Val-Val-Leu-Ile-Asn-Ala-Gln-Asn-G intramuscular and subcutaneous routes as well as by suppository. The compounds may be administered by any convenient route, for example by infusion or bolus injection and may be administered together with other biologically active agents. Administration is preferably systemic.

The present invention also provides pharmaceutical compositions. Such compositions comprise a therapeutically effective amount of the, and a pharmaceutically acceptable carrier or excipient. Such a carrier includes but is not limited to saline, buffered saline, dextrose, water, glycerol, ethanol, and combinations thereof. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampoule or sacbette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Pharmaceutical preparations can also often be administered rectally, using suppositories, particularly for sustained-release administration or administration to very young, old, infirm or those for whom other routes of administration present unusual obstacles. Suppository formulations include an appropriate amount of the compound(s)/composition(s) of the invention in a suppository base. Suitable suppository bases include natural or synthetic triglycerides or paraffin hydrocarbons. In addition, gelatin rectal capsules can be used whose base or excipient includes liquid triglycerides, polyethylene glycols, or paraffin hydrocarbons.

The therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The compound and composition are used in at least 5 µg/kg body weight and most generally need not be more than 500 µg/kg. Preferably, it is at least about 20 µg/kg and usually need not be more than about 100 µg/kg. The compound is typically administered for a period of at least about 7 days but generally not to exceed 30 days, with a typical therapeutic treatment period of 7 to 14 days. It will preferably be administered rectally by suppository, one to three times per day, and will be adjusted to meet optimal efficacy and pharmacological dosing.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

EXAMPLE 1

Isolation/Purification of Glycoprotein ALICIN

Fresh root tubers (1.0 kg) of the Zei-Bai plant (ZB) was obtained from local vendors of produce and farmers in the He-Nan Province, PRC. After the skin of the tuber was removed, its juice (approximately 200 ml) was extracted using a Panasonic Juice Extractor. The extract were chilled to 4° C. on an ice bath and adjusted to pH 4 by dropwise addition of 2M hydrochoric acid. While precipitates occured, slowly added 0.8 volume of the iced acetone to the chilled extracts. Centrifuge and discard the precipitates using Beckman Centrifuge at 4° C. and 3000 rpm for 20 minutes. Collect the supernantant and add slowly 80 ml of ice acetone to the supernantant until the precipitates was complete. Centrifuge and collect the precipitates (same protocol described above). The precipitates were dissolved in 10 ml double deionized (d.d.) water and then dialyzed against 10 volumes of d.d. water for 48 hours at 4° C. (3 changes in buffer). The undissolved precipitate was removed and the supernantant was collected by centrifugation as above. The protein solution was lyophilized (Labonco, Germany) to a dry powdered glycoprotein (1.2±0.3 g).

SDS-Page revealed one large protein band (85%) and three other minor bands. The large band has a molecular weight approximately 21 kD.

The above prepared lyophilisate was reconstituted to about 200 ml and maintained at 4° C. overnight. Observed precipitate was removed by centrifugation at 3000 rpm for 30 minutes at 4° C. The supernantant was loaded over a Ricinus communis Agglutinin affinity column (Sepharose 4B, 2.5×58 cm) which was prepared following the procedures of Dulaney (Mol. Cell. Biochem. 21, 43–63, 1978). The glycoprotein was displaced from the column with a carbohydrate buffer (0.1M phosphate and 0.2M galactose, pH 7.2). After lyophilization, about 1.0 g of the glycoprotein was obtained.

Both cellulose acetate membrane and SDS-PAGE showed that the glycoprotein prepared from this affinity column has a purity of >95%. The molecular weight observed was approximately 21 kD.

EXAMPLE 2

Purification of Polypeptide Protein PROTEINA

ALICIN was dissociated into the polypeptide component, PROTEINA, as follows. ALICIN (1.0 g) prepared as described above was dissolved in 20 ml solution composed of 8M urea and 0.1M phosphate buffer (pH 7.2). Centrifuge and discard the undissolved solid with the Beckman Centrifuge at 4° C., 3000 rpm for 20 minutes. Pass the supernantant through a CM Sepharose C-50 colum (5×53 cm), eluted the protein by applying 2L buffer of 8M urea and 0.1M phosphate at pH 7.2 and followed at pH 9 respectively. The flow rate was 36 ml/hr with each collected fraction of 1 ml per tube. The protein content was detected by 280 nm absorption. One large peak of the Protein was observed. The protein solution from each tube was polled and dialyzed against double distilled water for 48 hours at 4° C. with several buffer changes.

After removing precipitate by centrifugation at 3000 rpm for 20 min, the supernantant was dialized against barbital buffer (pH 8.6)at 4° C. for 24 hours with several buffer changes. The pure protein was obtained by crystalization with the barbital buffer. About 500 mg of the PROTEINA was obtained. SDS-Page showed one pure protein band (>98%) with a molecular weight approximately 15 kDa.

ANTIVIRAL AND ANTITUMOR AGENTS

The present invention relates to polypeptide-containing compound(s) (hereinafter "PROTEINA"), composition(s) comprising such compound(s) along with divalent metal ions and/or a carbohydrate moiety (hereinafter "ALICIN"), their antiviral and anti-hepatoma activities, and the enhancement of activity of antiviral polypeptide-containing agents by their combination with a carbohydrate and at least one divalent metal ion. Preferably, the carbohydrate is a polysaccharide that consists essentially of arabinose and galactose and, independently, the at least one divalent metal ion consists essentially of magnesium and zinc. The carbohydrate and divalent metal ion can be present in the form of a complex.

Thus, in one principal aspect, the invention relates to a composition comprising an amino acid-containing compound having the formula:

```
R—Thr—R—Gly—Asn—Tyr—R—Arg—Leu—R—Ala—Gly—
R—Leu—Arg—Glu—Asn—Ile—R—Leu—Gly—R—Leu—R—Ala—
Ile—R—Leu—R—Tyr—Tyr—R—Ile—Gln—R—Ser—Glu—Ala—
Ala—Arg—R—Ile—Glu—R—Arg—R—Ile—R—Asn—R—Gly—R—
Phe—R—Ser—Pro—R—Leu—R
``` wherein each R is independently at least one amino acid or analog thereof. Preferably, the compound has the formula:

```
Xaa—Xaa—Xaa—Thr—Xaa—Xaa—Xaa—Xaa—Gly—Asn—Tyr—
Xaa—Arg—Leu—Xaa—Xaa—Xaa—Ala—Gly—Xaa—Leu—Arg—
Glu—Asn—Ile—Xaa—Leu—Gly—Xaa—Xaa—Xaa—Leu—Xaa—
Xaa—Ala—Ile—Xaa—Xaa—Leu—Xaa—Tyr—Tyr—Xaa—Xaa—Xaa—
Xaa—Xaa—Xaa—Xaa—Xaa—Xaa—Xaa—Xaa—Xaa—Ile—Gln—
Xaa—Xaa—Ser—Glu—Ala—Ala—Arg—Xaa—Xaa—Xaa—Ile—Glu—
Xaa—Xaa—Xaa—Xaa—Xaa—Arg—Xaa—Xaa—Xaa—Xaa—Xaa—
Xaa—Xaa—Xaa—Xaa—Xaa—Xaa—Xaa—Xaa—Xaa—Xaa—Xaa—
Xaa—Xaa—Xaa—Xaa—Xaa—Xaa—Xaa—Xaa—Xaa—Xaa—Xaa—
Ile—Xaa—Xaa—Xaa—Asn—Xaa—Gly—Xaa—Phe—Xaa—Ser—Pro—
Xaa—Xaa—Leu—Xaa—Xaa—Xaa—Xaa—Xaa—Xaa—Xaa—Xaa—
Xaa—Xaa—
``` wherein each Xaa is independently a substantially homologous spacer or linker formed of at least one amino acid or analog thereof. Usually, each R is independently one or more amino acids. In a particularly preferred embodiment, the amino acid-containing compound has the formula:

```
Arg-Lys-Val-Thr-Leu-Pro-Tyr-Ser-Gly-Asn-Tyr-Glu-Arg-Leu-
Gln-Thr-Ala-Ala-Gly-Gly-Leu-Arg-Glu-Asn-Ile-Pro-Leu-Gly-
Leu-Pro-Ala-Leu-Asp-Ser-Ala-Ile-Thr-Thr-Leu-Phe-Tyr-Tyr-
Asn-Ala-Asn-Ser-Ala-Ala-Ser-Ala-Leu-His-Val-Leu-Ile-Gln-
Ser-Thr-Ser-Glu-Ala-Ala-Arg-Tyr-Lys-Phe-Ile-Glu-Gln-Gln-
Ile-Gly-Ser-Arg-Val-Asp-Lys-Thr-Phe-Leu-Pro-Ser-Leu-Ala-
Ile-Ile-Ser-Leu-Glu-Asn-Ser-Leu-Trp-Leu-Ala-Leu-Ser-Lys-
Gln-Ile-Gln-Ile-Ala-Ser-Thr-Asn-Asn-Gly-Thr-Phe-Glu-Ser-
Pro-Val-Val-Leu-Ile-Asn-Ala-Gln-Asn-Gln-Arg-Asn-Asn-His
```

In another aspect, the above composition(s) further include a carbohydrate. The carbohydrate can be a monosaccharide, i.e. $(CH_2O)_n$ where n is at least 3, preferably hexoses such as glucose, mannose, galactose and pentoses such as arabinose and the like or one or more of the known disaccharides. The carbohydrate can also be a homo- or hetero- polysaccharide. When the carbohydrate is a polysaccharide, it is preferably a homo- or hetero- polymer of glucose, mannose, arabinose, galactose or monosaccharide amine. A particularly preferred polysaccharide is one that consists essentially of arabinose and galactose, particularly in a weight ratio of about 1:0.05, respectively.

In another aspect, the composition further comprises at least one divalent metal ion. Preferably, the divalent metal ion is selected from the group consisting of magnesium and zinc. It is particularly preferred that they be present in a weight percent of about 4–20 and 2–10, respectively, of the total composition. Range of ratios between Mg and Zn is generally 1:1 to 3:1, preferably 2:1, and their over all weight percentage in the composition is 6–30 weight percent of the composition.

Another aspect of the invention relates to a method for treating a viral infection in an individual in need thereof which comprises administering a therapeutically effective amount of the composition(s). Particularly contemplated viral pathogens intended for treatment include Hepatitis A virus, Epstein-Barr and Influenza A viruses.

Another aspect of the invention relates to a method for treating a hepatoma in an individual in need thereof which comprises administering a therapeutically effective amount of the composition(s).

Another aspect of the invention relates to a composition which comprises the composition of an antiviral polypeptide-containing agent, such as one or more of the interferons, trichosanthin and others, in combination with a carbohydrate, particularly a carbohydrate such as those described above, and at least one divalent metal ion, particularly such as those described above. Preferably, the carbohydrate is a polysaccharide that consists essentially of arabinose and galactose and, independently, the at least one divalent metal ion consists essentially of magnesium and zinc.

As used herein, the term "substantially homologous" means that a particular subject sequence, for example, a sequence of amino acid analogs, varies from a reference sequence by one or more substitutions, deletions, or additions, the net effect of which does not result in an adverse functional dissimilarity between reference and subject sequences. For purposes of the present invention, sequences having greater than 90 percent homology, equivalent biological activity are considered substantially homologous. Sequences having lesser degrees of homology, but comparable bioactivity, are considered equivalents.

The PROTEINA polypeptide-containing portion of the ALICIN composition(s), its fragments or other derivatives, or analogs thereof, or cells expressing them can be used as an immunogen to produce antibodies thereto. These antibodies can be, for example, polyclonal, monoclonal, chimeric, single chain, Fab fragments, or an Fab expression library. Various procedures known in the art may be used for the production of polyclonal antibodies.

For preparation of monoclonal antibodies, any technique which provides antibodies produced by continuous cell line cultures can be used. Examples include the hybridoma technique (Kohler and Milstein, 1975, Nature 256:495–497), the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96). Techniques described for the production of single chain antibodies (U.S. Pat. No. 4,946,778) can be adapted to produce specific single chain antibodies.

The antibodies can be used in methods relating to the localization and activity of the protein sequences of the invention, e.g., for imaging these proteins, measuring levels thereof in appropriate physiological samples and the like.

Therapeutic Administration and Compositions

Modes of administration of the compound(s) and composition(s) include but are not limited to intravenous, Determine the serum dilution which leads to a 50% cell infection. This serum dilution was found to be 1:45 and was used as the control sample and for all other samples prepared below.

5) Prepare 48 samples containing HAV-serum-hepatic cells according to the protocols of step 3 except that the serum dilution used is determined at step 4 (i.e. 1:45). The samples were divided into 6 groups, and each group had 8 identical tubes. The six groups are defined below:

Group 1: control samples.

Group 2: control samples added with 400 ug of 85% pure ALICIN.

Group 3: control samples added with 400 ug of pure PROTEINA.

Group 4: Control samples added with 400 ug of combination (200 ug pure PROTEINA, 104 ug polysacchrides (prepared in example 4) and 96 ug divalent metals prepared in example 5).

Group 5: Control samples added with 96 ug of divalent metals.

Group 6: Control samples added with 104 ug of polysacchrides.

6) Incubate all 48 samples in an incubator (5% CO2) at 37° C. for 10 days. Examine and count infected hepatic cells of each tube using Olympus phase contrast microscope daily. At the end of tenth day, the experiments were stoped. Results of each group are compared to the control group as shown in Table 2.

TABLE 2

| Group | Tubes infected | % Infection | Efficacy |
|---|---|---|---|
| 1 | 5/8 | 72.5 | 0% |
| 2 | 1/8 | 12.5 | 839% |
| 3 | 2/8 | 25.0 | 66% |
| 4 | 0/8 | 0.0 | 100% |
| 5 | 3/8 | 37.5 | 48% |
| 6 | 4/8 | 50.0 | 31% |

Table 2 clearly shows that all 5 formulations inhibit the growth of HAV. Especially, PROTEINA combination formula can irreversibly neutralize the virus completely in-vitro at 400 ug. The ALICIN (85%) at the same concentration can neutralize virus up to 83% and the PROTEINA at the same dosage can neutralize virus up to 66%. These results lead us to the choice of the combination formula for further study.

EXAMPLE 7

Anti-Epstein-Barr Virus Activity

1) Preparation of lymphocyte cells:

Collect ten tubes of 8 ml human cord blood and add equal volume of Hank's solution (pH7.5) for dilution. White blood cells were separated from red blood cells by sucrose density method.

After washing the separated white cells twice with Hank's solution, the white cell suspension was transfered to a glass dish and incubated on water bath at 37° C. for 40 minutes. Most of the monocytes were adhered to the glass wall. Remove lymphocyte cells. Twenty test tubes containing lymphocyte cells were prepared. Each tube had 1 ml of cell solution and a cell concentration of $2\times10^6$/ml.

2) Preparation of lymphocyte samples containing Epstein-Barr Virus (EBV):

EBV suspension (200TCD50) was purchaed from Center of China Preventive Medicine. 0.1 ml of EBV suspension was added to the above prepared 20 lymphocyte tubes (step 1).

3) Divide the above 20 lymphacyte tubes (prepared in step 2) into 4 groups, each group has 5 identical samples, The four groups are defined below:

group 1: Control group, samples prepared in step 2.

group 2: Irradiation of EBV with X-ray (4000 R) for 1 minute before added to lymphocyte tubes.

group 3: 200 ug of the combined formula of PROTEINA +polysacchride +divalent metals was added to lymphocyte tubes.

group 4: 400 ug of the combined formulation of PROTEINA +polysaccharide +divalent metals was added to lymphocyte tubes.

All tubes from group 1 to 4 were incubated in a cell incubator (5% $CO_2$) at 37° C. until approximately 50% lymphocytes in the control group showed infection counted by Olympus phase contrast microscope. At this point, stop cell incubation and record the results of all tubes. They are summerized in Table 3.

TABLE 3

| Group | Average infection (%) | Efficacy (%) |
|---|---|---|
| 1 | 51.8 ± 3.6 | 0 |
| 2 | 2.4 ± 1.8 | 100 |
| 3 | 13.6 ± 3.2 | 74 |
| 4 | 1.2 ± 1.0 | 100 |

These results demonstrate that the PROTEINA combinaton formula completely neutralizes EBV at 400 ug. Its efficacy is comparable to that of X-ray.

EXAMPLE 8

Anti-Hepatoma(Human) Activity

Human hepatoma cell line (BEL-7402) was purchased from Shanghai Cell Biology Institute. Cells were removed from the medium in which they were provided, suspended in solution A(2.0 ml; 0.25% trypsin, 0.02% EDTA, 8 g/L of NaCl, 0.2 g/L KCl, 1.56 g/L $Na_2HPO_4.H_2O$, 0.2 g/L $KH_2PO_4$), maintained at room temperature for 1 minute, transferred to culture solution B, mixed thoroughly for 2 minutes and adjusted as necessary to suspension concentration of $10^4$ cells/ml. The composition of culture solution B was as follows: DMEM cell culture solution (Sigma, St. Louis, Mo.), 15% fetal calf serum, 50 u streptomycin, 50 u penicillin. This suspension was used as the control.

2) Divide 125 ml BEL-7402 cell suspension from step 1 into 25 bottles and 5 groups. Each group consists of 5 bottles (5 ml/bottle).

group 1 control solution of BEL-7402 cell suspension group 2 control solution added with 10 ug PROTEINA combination agent (see example 6)

group 3 control solution added with 40 ug PROTEINA combination agent.

group 4 control solution added with 80 ug PROTEINA combination agent.

group 5 control solution added with 100 ug PROTEINA combination agent.

3) Incubate all bottles in a cell incubator (5% CO2, 37° C.) for 3 days. Examine and count cell numbers at day 1, 2 and 3. The results observed are set forth in Table 4.

TABLE 4

| Group | cell count (x10 4/ml) | | | |
|---|---|---|---|---|
| | 0 | 24 hr | 48 hr | 72 hr |
| 1 | 4.5 ± 0.5 | 8.6 ± 0.9 | 20.0 ± 1.1 | 28.5 ± 2.4 |
| 2 | 4.5 ± 0.5 | 8.3 ± 0.9 | 19.5 ± 1.4 | 28.0 ± 2.1 |
| 3 | 4.5 ± 0.5 | 6.6 ± 0.6 | 12.5 ± 1.0 | 19.4 ± 1.8 |
| 4 | 4.5 ± 0.5 | 5.8 ± 0.5 | 10.0 ± 0.9 | 12.6 ± 1.4 |
| 5 | 4.5 ± 0.5 | no data | 9.8 ± 1.1 | 11.3 ± 1.2 |

It is clear that the PROTEINA combination formula can effectively inhibit the growth of hepatoma. The inhibition activity increases with the concentration, reaching saturation at 100 ug.

EXAMPLE 9

Comparison of Anti-HAV Activities of ALICIN (>95% pure), PROTEINA and Trichosanthin The protein trichosanthin has abortifacient, antitumor, ribosome inactivation, anti-HIV, immunomodulatory and insulin-like activities. Trichosanthin is a nonmetallo- and nonglyco- protein of 234 amino acids with an N-terminal aspartate and an carboxy terminal alanine. In arriving at the present invention it has been observed by the inventor that a selected partial amino acid sequence of trichosanthin starting from 108 (arginine) to 158 (leucine) and from 160 (valine) to 232 (asparagine) are homologous to the major part of PROTEINA: from amino acid 1 (arginine) to 51 (leucine) and 53 (valine) to 125 (asparagine).

Seventy samples containing HAV-serum-hepatic cells (BEL-7405) were prepared according to the protocol of Example 7. They were divided into 7 groups of 10 samples each as follows.
Group 1: control group (untreated cells)
Group 2: sample plus 300 ug of ALICIN (>95%);
Group 3: sample plus 200–300 ug of PROTEINA (>99%);
Group 4: sample plus 200–300 ug of trichosanthin;
Group 5: sample plus 100–300 ug of zinc glucose;
Group 6: sample plus 200 ug of PROTEINA and 100 ug of zinc glucose;
Group 7: sample plus 200 ug of trichosanthin and 100 ug of zinc glucose;

Following the same protocols of example 7, the incubation and microscopic examination were carried out for 10 days. The results are summarized in Table 5.

TABLE 5

| Group | Tubes infected | % Infection | Efficacy |
|---|---|---|---|
| 1 | 5/10 | 50 | 0 |
| 2 | 0/10 | 0 | 100 |
| 3 | 2/10 | 20 | 80 |
| 4 | 3/10 | 30 | 70 |
| 5 | 3/10 | 30 | 70 |
| 6 | 1/10 | 10 | 90 |
| 7 | 1/10 | 10 | 90 |

These data show that pure ALICIN has similar potency as that of the PROTEINA combination formula. Each of them irreversibly neutralizes the HAV. PROTEINA alone, rather than in combination with the carbohydrate and divalent metal, is less potent than ALICIN, but more potent than trichosanthin. However, the combination of PROTEINA with zinc glucose provided a composition of enhanced antiviral activity.

Similarly, enhancement in potency of trichosanthin was observed when combined with zinc glucose. Since zinc glucose contains both the carbohydrate and divalent metal, these results clearly indicate that adding sugar and divalent metal to the antiviral protein solution significantly enhances the antiviral activity of the proteins which do not contain sugar or metal or both. These results are in agreement with the data demonstrated in example 6.

EXAMPLE 10

In-vivo anti-Influenza A3 Virus (IAV) activities

A total of 90 Kun-Min white mice (body weight 20 ±1), with 50% male and female each, were divided into 9 groups. Each group had 10 identical mice. They are defined below:

Group 1: control group, abdominal injection of 0.5 ml of saline solution (0.9% NaCl) 2 hours prior to tail vein injection of IAV;

Group 2: same as 1, except 4 hour prior to injection of IAV.

Group 3: treated group, abdominal injection of 0.5 ml of the Proteina Combination Formula(400 ug) 2 hours prior to tail vein injection of IAV.

Group 4: Same as 3, except 4 hours prior to injection of IAV.

Group 5: Same as 3, except 6 hours prior to injection of IAV.

Group 6: Same as 3, except 10 hours prior to injection of IAV.

Group 7: Same as 3, except 18 hours prior to injection of IAV.

Group 8: Same as 3, except 24 hours prior to injection of IAV.

Group 9: Same as 3, except 48 hours prior to injection of IAV.

2) Preparation of Influenza A3 Virus solution:

Influenza A3 Virus (Jinfong-75-39) was purchased from Center of China Preventive Medicine. It was multiplied in chick embryo (10 days old) at 37° C. for 40 hours. The allantoic fluid containing $10^{-8}$ titer of the virus was harvested from the chick embryo.

The obtained allantoic fluid was centrifuged at 4000 rpm for 30 minutes to remove large particulates. The supernatant was mixed with a final concentration of 3.5% chick red blood cells (prefixed by formaldehyde) and stored at 4° C. overnight. After centrifugation at 2000 rpm for 10 minutes, the precipitated RBCs and viruses were washed twice with cold (0° C.) saline solution and centrifuged. Appropriate amount (⅕ volume of the original allantoic fluid) of 0.01M phosphate buffer (pH 7.8) was added to RBCs and viruses and incubated at 37° C. water bath for 3 hours before centrifugation (2000 rpm for 10 min). Save the supernatant which contained the viruses. Added 100 volume (of the original allantoic fluid) of phosphate buffer to RBCs and incubated at 37° C. for 2 hours. Centrifuged again. Combined the two supernatant which contained viruses and recentrifuged at 4000 rpm for 30 minutes to remove residual RBCs. Applied 20 ml of the supernatant to a Sephadex G200 column (2.5 cm×60 cm, flow rate 40 ml/hr) preequilibrated with the phosphate buffer (0.01M). Centrifuged the virus solution (collected from the column) at 2800 rpm for 60 minutes. Discarded the supernatant. Added 2 ml of the phosphate buffer to the virus precipitate and dispersed the virus suspension. Added more phosphate buffer untill the volume of the virus suspension was ¹⁄₃₀₀ volume of the the original allantoic fluid. Homogenized the suspension by sonication for 1–2 minutes. The virus solution was ready for use.

3) Vein injection of 0.25 ml of the virus solution to each tail of mice following the protocol of step 1.

4) Observed and recorded the number of mice died in 5 days after the virus injection.

The results are summarized in Table 6:

TABLE 6

| Group | sample # | # Death | % death |
|-------|----------|---------|---------|
| 1 | 10 | 9 | 90 |
| 2 | 10 | 10 | 100 |
| 3 | 10 | 7 | 70 |
| 4 | 10 | 5 | 50 |
| 5 | 10 | 5 | 50 |

TABLE 6-continued

| Group | sample # | # Death | % death |
|-------|----------|---------|---------|
| 6 | 10 | 5 | 50 |
| 7 | 10 | 5 | 50 |
| 8 | 10 | 3 | 30 |
| 9 | 10 | 9 | 90 |

The results indicate that the combination agent can effectively reduce the infectiousness of the Influenza Virus A3. In view of the seriousness of the i.v. infection of the virus, it is encouraging to see that the motility rate can be reduced at least to half if the invention composition was injected to mice at least 4 hours in advance.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
    ( A ) LENGTH: 126 amino acids
    ( B ) TYPE: amino acid
    ( D ) TOPOLOGY: linear ( i i ) MOLECULE TYPE: peptide ( v i ) ORIGINAL SOURCE:
    ( A ) PLANT: Zei-Bai ( v i i ) FEATURE:
    ( A ) NAME/KEY: PROTEINA peptide ( x i ) SEQUENCE DESCRIPTION: SEQ ID NO: 1:

```
Arg Lys Val Thr Leu Pro Tyr Ser Gly Asn Tyr Glu Arg Leu
              5                   10

Gln Thr Ala Ala Gly Gly Leu Arg Glu Asn Ile Pro Leu Gly
 15              20                   25

Leu Pro Ala Leu Asp Ser Ala Ile Thr Thr Leu Phe Tyr Tyr
     30              35                       40

Asn Ala Asn Ser Ala Ala Ser Ala Leu His Val Leu Ile Gln
         45              50                       55

Ser Thr Ser Glu Ala Ala Arg Tyr Lys Phe Ile Glu Gln Gln
             60              65                       70

Ile Gly Ser Arg Val Asp Lys Thr Phe Leu Pro Ser Leu Ala
                 75                   80

Ile Ile Ser Leu Glu Asn Ser Leu Trp Leu Ala Leu Ser Lys
 85                   90                   95

Gln Ile Gln Ile Ala Ser Thr Asn Asn Gly Thr Phe Glu Ser
     100                 105                 110

Pro Val Val Leu Ile Asn Ala Gln Asn Gln Arg Asn Asn His
         115                 120                 125
```

( 2 ) INFORMATION FOR SEQ ID NO:2:

( i ) SEQUENCE CHARACTERISTICS:

-continued

```
( A ) LENGTH: 126 amino acids
( B ) TYPE: amino acid
( D ) TOPOLOGY: linear ( i i ) MOLECULE TYPE: peptide ( v i ) ORIGINAL SOURCE:
        ( A ) SYNTHETIC ( v i i ) FEATURE:
        ( A ) NAME/KEY: PROTEIN A peptide analog 1

( x i ) SEQUENCE DESCRIPTION: SEQ ID NO: 2:

Xaa  Thr  Xaa  Xaa  Xaa  Xaa  Gly  Asn  Tyr  Xaa  Arg  Leu  Xaa  Ala
                         5                      10

Gly  Xaa  Leu  Arg  Glu  Asn  Ile  Xaa  Leu  Gly  Xaa  Xaa  Xaa  Leu
 15                       20                       25

Xaa  Xaa  Ala  Ile  Xaa  Xaa  Leu  Xaa  Tyr  Tyr  Xaa  Xaa  Xaa  Xaa
      30                  35                       40

Xaa  Xaa  Xaa  Xaa  Xaa  Xaa  Xaa  Xaa  Ile  Gln  Xaa  Xaa  Ser  Glu
           45                      50                       55

Ala  Ala  Arg  Xaa  Xaa  Xaa  Ile  Glu  Xaa  Xaa  Xaa  Xaa  Xaa  Arg
               60                       65                       70

Xaa  Xaa  Xaa  Xaa  Xaa  Xaa  Xaa  Xaa  Xaa  Xaa  Xaa  Xaa  Xaa  Xaa
                    75                       80

Xaa  Xaa  Xaa  Xaa  Xaa  Xaa  Xaa  Xaa  Xaa  Xaa  Xaa  Xaa  Xaa  Ile
 85                            90                       95

Xaa  Xaa  Xaa  Asn  Xaa  Gly  Xaa  Phe  Xaa  Ser  Pro  Xaa  Xaa  Leu
     100                 105                      110

Xaa  Xaa  Xaa  Xaa  Xaa  Xaa  Xaa  Xaa  Xaa  Xaa  Xaa  Xaa  Xaa  Xaa
          115                      120                      125
```

What is claimed is:

1. A composition which comprises a compound having the amino acid sequence

Arg Lys Val Thr Leu Pro Tyr Ser Gly Asn Tyr Glu Arg Leu
Gln Thr Ala Ala Gly Gly Leu Arg Glu Asn Ile Pro Leu Gly
Leu Pro Ala Leu Asp Ser Ala Ile Thr Thr Leu Phe Tyr Tyr
Asn Ala Asn Ser Ala Ala Ser Ala Leu His Val Leu Ile Gln
Ser Thr Ser Glu Ala Ala Arg Tyr Lys Phe Ile Glu Gln Gln
Ile Gly Ser Arg Val Asp Lys Thr Phe Leu Pro Ser Leu Ala
Ile Ile Ser Leu Glu asn Ser Leu Trp Leu Ala Leu Ser Lys
Gln Ile Gln Ile Ala Ser Thr Asn Asn Gly Thr Phe Glu Ser
Pro Val Val Leu Ile Asn Ala Gln Asn Gln Arg Asn Asn His having magnesium and zinc divalent ions complexed therewith.

2. The composition of claim 1 wherein the magnesium and zinc are present in the composition in a weight percent of about 4–20 and 2–10, respectively.

3. The composition of claim 1 which further comprises a carbohydrate.

4. A method for treating a viral infection in an individual in need thereof which comprises administering a therapeutically effective amount of the composition of claim 3.

5. A method for treating hepatoma in an individual in need thereof which comprises administering a therapeutically effective amount of the composition of claim 3.

6. A composition which comprises an antiviral effective amount of a compound having the amino acid sequence Arg Lys Val Thr Leu Pro Tyr Ser Gly Asn Tyr Glu Arg Leu
Gln Thr Ala Ala Gly Gly Leu Arg Glu Asn Ile Pro Leu Gly
Leu Pro Ala Leu Asp Ser Ala Ile Thr Thr Leu Phe Tyr Tyr
Asn Ala Asn Ser Ala Ala Ser Ala Leu His Val Leu Ile Gln
Ser Thr Ser Glu Ala Ala Arg Tyr Lys Phe Ile Glu Gln Gln
Ile Gly Ser Arg Val Asp Lys Thr Phe Leu Pro Ser Leu Ala
Ile Ile Ser Leu Glu asn Ser Leu Trp Leu Ala Leu Ser Lys
Gln Ile Gln Ile Ala Ser Thr Asn Asn Gly Thr Phe Glu Ser
Pro Val Val Leu Ile Asn Ala Gln Asn Gln Arg Asn Asn His which is complexed with a carbohydrate moiety and divalent magnesium and zinc ions.

7. The composition of claim 6 wherein the carbohydrage moiety is a polysaccharide that consists essentially of arabinose and galactose.

* * * * *